(12) United States Patent
Friedman et al.

(10) Patent No.: US 7,204,808 B1
(45) Date of Patent: Apr. 17, 2007

(54) APPARATUS, SYSTEM AND METHOD FOR COLLECTING NON-INVASIVE BLOOD PRESSURE READINGS

(75) Inventors: Bruce A. Friedman, Tampa, FL (US); John Booth, Tampa, FL (US); John P. Clemmons, Tampa, FL (US)

(73) Assignee: The General Electric Company, Schenectady, NY (US)

(\*) Notice: Subject to any disclaimer, the term of this patent is extended or adjusted under 35 U.S.C. 154(b) by 0 days.

(21) Appl. No.: 11/249,593

(22) Filed: Oct. 13, 2005

(51) Int. Cl.
*A61B 5/00* (2006.01)

(52) U.S. Cl. ................. 600/490; 600/494; 600/496

(58) Field of Classification Search .................. None
See application file for complete search history.

(56) References Cited

U.S. PATENT DOCUMENTS

| | | | |
|---|---|---|---|
| 5,144,956 A * | 9/1992 | Souma | 600/495 |
| 5,553,622 A * | 9/1996 | McKown et al. | 600/505 |
| 5,715,831 A * | 2/1998 | Johnson | 600/539 |
| 2003/0060721 A1* | 3/2003 | Nakazawa et al. | 600/490 |
| 2003/0173408 A1 | 9/2003 | Mosher, Jr. et al. | |
| 2003/0174049 A1 | 9/2003 | Beigel et al. | |
| 2005/0083527 A1* | 4/2005 | Flaherty et al. | 356/437 |
| 2005/0101843 A1* | 5/2005 | Quinn et al. | 600/300 |

\* cited by examiner

*Primary Examiner*—Robert Nasser
(74) *Attorney, Agent, or Firm*—Andrus, Sceales, Starke & Sawall, LLP

(57) ABSTRACT

An apparatus, system and method for collecting non-invasive blood pressure readings from a patient is provided. A non-invasive blood pressure cuff is arranged to be worn about a wrist of a patient and to be operatively connected to a blood pressure monitor. Communication means are operatively connected to the blood pressure cuff the monitor and arranged to automatically communicate a parameter associated with the cuff to the monitor. The monitor is arranged to automatically adjust blood pressure algorithms based upon the parameter to enhance the accuracy of blood pressure readings.

11 Claims, 2 Drawing Sheets

APPARATUS, SYSTEM AND METHOD FOR COLLECTING NON-INVASIVE BLOOD PRESSURE READINGS

BACKGROUND OF THE INVENTION

The present invention relates to an apparatus, system and method for collecting non-invasive blood pressure readings from a patient.

Blood pressure is a vital sign that is measured on patients in medical settings. Blood pressure readings are most often taken using a non-invasive cuff attached to the upper arm of the patient. The cuff is operatively connected to a blood pressure monitor, which receives readings from the cuff, analyzes the readings using various predetermined algorithms, and displays values associated with the blood pressure of the patient.

Problems with known apparatus, systems and methods for taking non-invasive blood pressure measurements result from the use of incorrectly sized blood pressure cuffs to obtain blood pressure values. For example, many facilities use a single cuff for all patients in a particular ward or unit. If the cuff is not the appropriate size for a particular patient, inaccurate measurements may result. If a common cuff is utilized, there is also the serious risk of cross-contamination between patients.

It is therefore desirable to provide an apparatus, system and method for collecting non-invasive blood pressure readings that minimizes the use of incorrectly-sized blood pressure cuffs in the medical setting. It is also desirable to improve the performance of non-invasive blood pressure monitors by providing means for determining blood pressure that accounts for physical and/or operational attributes associated with different blood pressure cuffs carried by different respective patients. It is further desirable to provide such an apparatus, system and method that can easily communicate with existing electronic medical records at operating medical facilities. It is further recognized as desirable to provide such an apparatus, system and method that facilitates quick and accurate communication of patient identification information for each patient and associated blood pressure cuff in the medical setting.

SUMMARY OF THE INVENTION

The present application describes such an apparatus, system and method for obtaining non-invasive blood pressure readings. In one example, a non-invasive blood pressure cuff is arranged to be worn about a limb of the patient and to be operatively connected to a blood pressure monitor. Electronic communication means associated with the cuff and monitor are arranged to automatically communicate a parameter associated with the cuff to the monitor. The monitor is arranged to automatically adjust at least one of its operational characteristics, such as for example its blood pressure analysis algorithms, based upon the parameter to prove more accurate blood pressure readings.

In another example, the monitor is placed in communication with existing electronic medical records systems associated with a medical facility. The electronic medical records can thus be updated in real-time based upon non-invasive blood pressure readings.

In a further example, the wrist-worn blood pressure cuff can be provided with patient identification information, which, when communicated to the monitor, further enhances the ability to update electronic medical records associated with the medical facility.

In yet another example, a system for taking non-invasive blood pressure values from a patient includes a non-invasive blood pressure monitor, a non-invasive blood pressure cuff operatively connected to the monitor and worn on a limb of the patient. The cuff and monitor have means for automatically communicating at least one parameter associated with the cuff to the monitor. The monitor is arranged to automatically adjust an operational characteristic based upon the parameter associated with the cuff. For example, the monitor can be arranged to factor the cuff parameter into a blood pressure analysis algorithm to obtain a more accurate blood pressure reading.

A method is also provided wherein non-invasive blood pressure readings from a plurality of patients in a healthcare setting are collected by: (1) providing each patient with a correctly-sized, dedicated, non-invasive blood pressure cuff arranged to be worn about a limb of the patient and operatively connected to a non-invasive blood pressure monitor; (2) assigning a cuff parameter to each blood pressure cuff, the cuff parameter identifying a physical and/or operational attribute of the respective cuff; (3) automatically communicating the cuff parameter to the monitor; and (4) automatically adjusting an operational characteristic of the monitor based upon the cuff parameter to optimize non-invasive blood pressure readings taken by the respective cuff.

In general, the apparatus, system and method make it possible to provide a dedicated, possibly disposable, non-invasive blood pressure cuff that is properly sized to each individual patient receiving care in a particular medical setting. The apparatus, system and method advantageously facilitates enhanced analysis by the blood pressure monitor to provide more accurate blood pressure readings.

BRIEF DESCRIPTION OF THE DRAWINGS

The best mode of carrying out the invention is set forth with reference to the enclosed drawing figures wherein.

DETAILED DESCRIPTION OF THE PREFERRED EMBODIMENTS

In preferred embodiments of the present invention described in detail below, an apparatus, system and method for collecting non-invasive blood pressure readings from a patient is provided. It should be understood that the drawings and specification are to be considered an exemplification of the principles of the invention, which is more particularly defined in the appended claims. For example, although specific embodiments of a blood pressure cuff and non-invasive blood pressure monitor are depicted in the Figures, it will be recognized that different types of blood pressure cuffs and monitors could be used while employing the principles of the present invention. In addition, although the Figures depict particular steps related to the method of the invention, it will be recognized that alternative, equivalent steps or procedures may be employed within the principles of the claimed invention.

Figure 1:
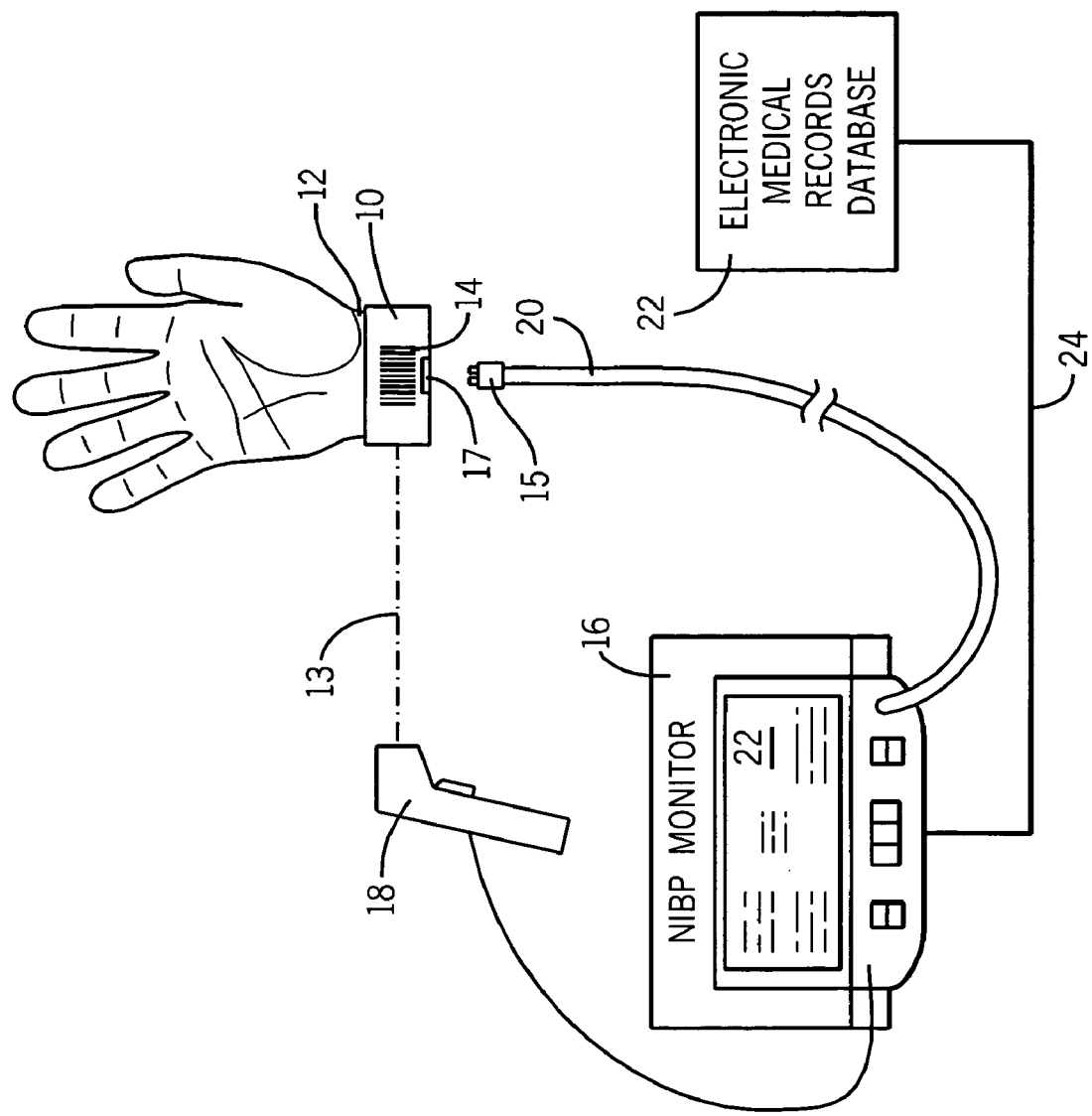
FIG. 1 is an illustrative view of a wrist-worn blood pressure cuff, a non-invasive blood pressure monitor, and an electronic medical records database.

Referring to FIG. 1, a non-invasive blood pressure cuff 10 is shown, as worn about the wrist 12 of a patient. As will be apparent from the description below, such a blood pressure cuff 10 can be provided to each patient in the medical setting in the same manner as, or instead of, conventional patient medical identification bracelets. In this manner, the blood pressure cuff 10 advantageously minimizes the chance for cross-contamination amongst patients, which is more likely when a common blood pressure cuff is utilized. It will also be recognized by those skilled in the art that alternative embodiments of blood pressure cuffs arranged to be worn about different areas of the patient's body can be utilized according to the principles of the present invention.

As shown in FIG. 1, the blood pressure cuff 10 is operatively or pneumatically connected to the blood pressure monitor 16 via an air hose 20. In the embodiment shown, the distal end of the air hose 20 has a plug 15 arranged to be removably received in a corresponding port 17 on the blood pressure cuff 10. An airtight seal is formed between the plug 15 and port 17 to pneumatically connect the hose 20 and monitor 16 to the cuff 10. Such arrangement enables the blood pressure monitor 16 to receive and analyze pressure readings from the blood pressure cuff 10 using various algorithms. It will be recognized by those skilled in the art that alternate means for physically and/or operatively connecting the hose 20 and cuff 10 can be employed within the scope of the present invention.

The blood pressure cuff 10 also includes communication means 14 arranged to carry a parameter associated with the cuff 10. Complementary communication means 18 are provided and are associated with a non-invasive blood pressure monitor 16. The communication means 14 and 18 are arranged to automatically communicate the cuff parameter to the monitor 16, as will be discussed further below.

The communication means 14 may include a pre-printed barcode, a radio frequency identification tag, or other means for communicating with the complementary communication means 18. In the illustrated embodiment, the communication means 14 includes a pre-printed barcode. The communication means 18 may include a barcode reader, a radio frequency transceiver, or other means for automatically communicating with the electronic communication means 14. In the illustrated embodiment, the communication means 18 includes a barcode reader. In general, communication means 14, 18 can include any means for providing an automatic communication between the cuff 10 and the monitor 16 via a wired or wireless communication link 13.

As stated above, the communication means 14 on the cuff 10 is arranged to carry at least one parameter associated with the cuff 10. The parameter may include information such as a physical characteristic of the cuff 10 or an operational quality of the cuff 10. In use, the cuff parameter is communicated by communication means 14 and communications means 18 to the monitor 16. The monitor 16 is arranged to receive the cuff parameter and thereafter adjust an operational characteristic of the monitor 16 based upon the received parameter. For example, in one arrangement the monitor 16 is arranged to incorporate the cuff parameter as a factor in its blood pressure algorithms to provide more accurate blood pressure readings. In another example, the monitor 16 is arranged to adjust its operating procedure to take more accurate reading from the particular patient based upon the particular blood pressure cuff parameter.

By providing automatic communication of the cuff parameter to the pressure monitor 16, the monitor 16 is more capable of performing enhanced analysis and thereby obtains and displays more accurate blood pressure readings. For example, based upon information such as the size and/or type of blood pressure cuff, the operational algorithm(s) is enhanced to acquire blood pressure measurements that are more accurate.

The communication means 14 on the blood pressure cuff 10 can also carry a patient parameter comprising data associated with the patient. Such information is communicated to the monitor 16 via the communication link 13 and communication means 18. Such a patient parameter could include identification information for the patient, or medical information associated with the patient such as, for example, historical blood pressure readings. According to this example, each cuff 10 worn by a patient can be programmed with identity and/or medical information specific to that individual patient. This patient parameter can thus be conveyed to the monitor 16.

In the illustrated embodiment, the blood pressure monitor 16 is further arranged to automatically communicate with an electronic medical records database 22 associated with the particular medical setting. Electronic medical records databases are commonly used in medical facilities to store and communicate information related to the facility, medical staff, and/or patients currently or previously treated at the facility. Automatic communication between the monitor 16 and the electronic medical records database 22 is provided by communication link 24, which may comprise any one of a variety of known electronic communication links such as a wireless radio frequency link or a wired link.

By providing automatic communication of values contained in the blood pressure monitor 16 to the electronic medical records database 22, medical staff are advantageously provided with real-time data regarding the blood pressure and/or identity and medical information for each particular patient in the medical setting.

Figure 2:
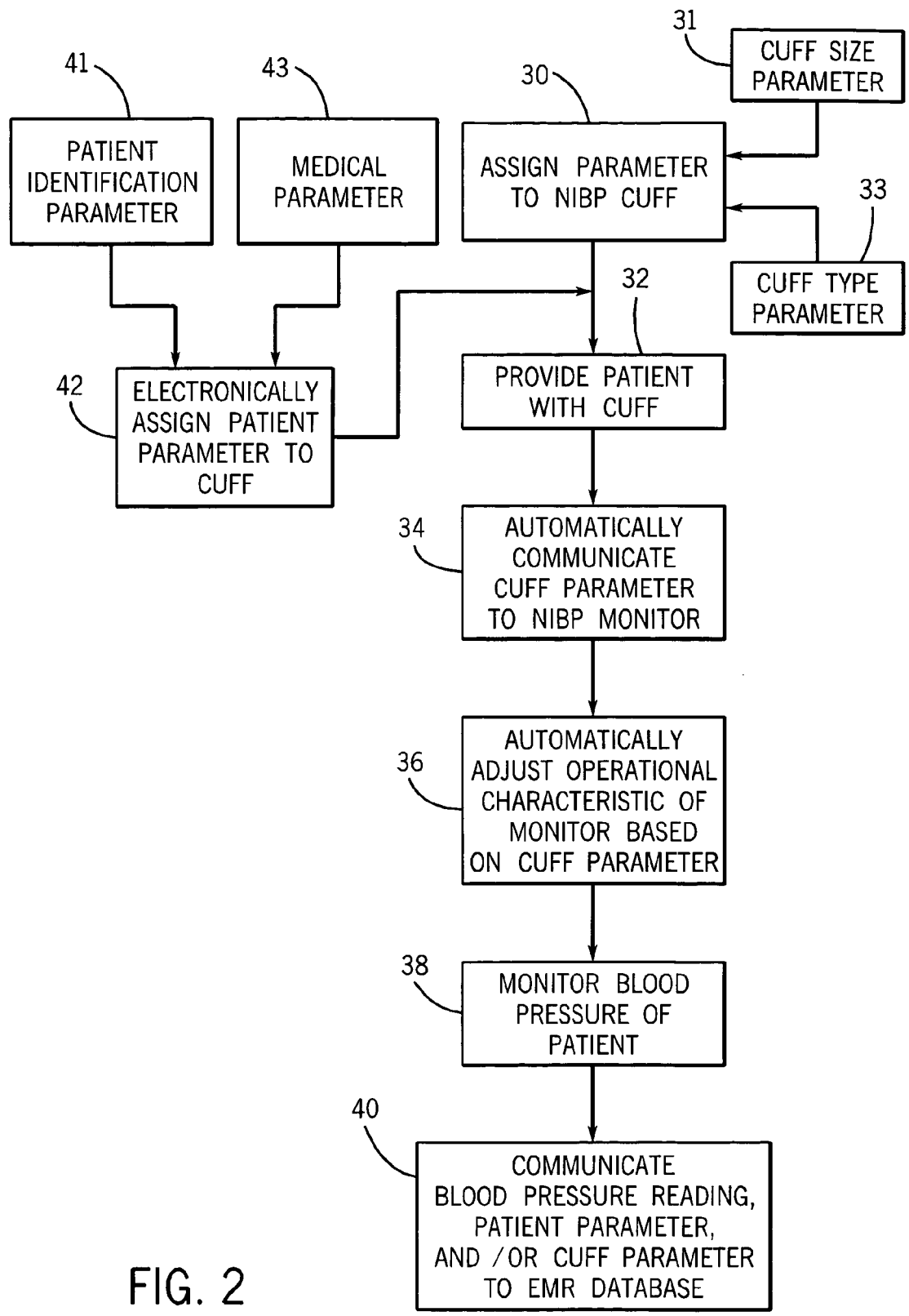
FIG. 2 is a flow chart illustrating one example of steps in a method of collecting non-invasive blood pressure readings.

Referring now to FIG. 2, the arrangement shown in FIG. 1 has been found to be useful in medical settings, such as hospital settings, where a plurality of patients having different body types and sizes are present. According to step 30, a cuff parameter such as, for example, cuff size 31 or cuff type 33 is assigned to each blood pressure cuff 10. It will be recognized by those skilled in the art that the cuff parameter could be any useful physical or operational information regarding the particular cuff 10 that the monitor 16 can utilize to increase the efficiency and/or accuracy of operations/algorithms run by the monitor 16.

At step 32, each patient is provided with a dedicated, correctly sized non-invasive blood pressure wrist cuff 10 that contains communication means 14 for providing the cuff parameter to associated communication means 18 on the monitor 16.

At step 34, the cuff parameter is automatically communicated to the non-invasive blood pressure monitor 16 for inclusion in related algorithms conducted by the monitor 16 to arrive at more accurate values associated with the blood pressure of the patient.

At step 36, the blood pressure monitor 16 is arranged to automatically adjust an operational characteristic based upon the cuff parameter received from the communication means 14. Thereafter, when the blood pressure of the patient is monitored at step 38, the adjusted operational characteristic will advantageously enhance the value obtained from the analysis performed at the monitor 16.

At step 40, the blood pressure reading(s) and or cuff parameter(s) collected by the monitor 16 are communicated to the electronic medical records database 22 existing at the respective hospital or healthcare setting. Such information can be provided in real time and is useful in updating patient records and providing up-to-the-minute information to caregivers throughout the hospital. This is illustratively shown at step 40.

The correctly sized, non-invasive blood pressure wrist cuff 10 can also carry a patient identification parameter 41 or medical parameter 43 associated with the particular patient wearing the cuff. As shown at step 42, when each patient receives a dedicated cuff, the patient parameter 41, 43 is assigned to the cuff. Thereafter, the communication means 14, 18 are arranged to automatically communicate the patient parameter to the monitor 16 at step 32 and the electronic medical records database 22 at step 40.

While this invention is susceptible to embodiments in many different forms, the drawings and specification describe in detail preferred embodiments of the invention. They are not intended to limit the broad aspects of the invention to the embodiments illustrated.

What is claimed is:

1. A system for providing non-invasive blood pressure values for a patient, the system comprising:
    a non-invasive blood pressure monitor; and
    a non-invasive blood pressure cuff arranged to be operatively connected to the monitor and to be worn on a limb of a patient, wherein the cuff and monitor comprise communication means for automatically communicating at least one parameter associated with a physical attribute of the cuff to the monitor;
    wherein the monitor is arranged to automatically adjust a blood pressure analysis algorithm of the monitor based upon the parameter associated with the cuff.

2. The system of claim 1, wherein the communication means comprises an electronic barcode associated with the cuff and a barcode reader associated with the monitor.

3. The system of claim 1, wherein the communication means comprises a radio frequency transceiver associated with the cuff and a radio frequency transceiver associated with the monitor.

4. The system of claim 1, wherein the communication means is arranged to automatically communicate at least one parameter associated with the patient to the monitor.

5. The system of claim 4, wherein the at least one patient parameter comprises medical data associated with the patient.

6. The system of claim 4, wherein the at least one patient parameter comprises identification information for the patient.

7. A method of collecting non-invasive blood pressure readings from a plurality of patients in a healthcare setting, the method comprising the steps of:
    providing each patient with a dedicated non-invasive blood pressure cuff arranged to be worn about a limb of the patient and operatively connected to a non-invasive blood pressure monitor;
    assigning a cuff parameter to each blood pressure cuff, the cuff parameter identifying a physical attribute of the respective cuff;
    automatically communicating the cuff parameter to the monitor; and
    automatically adjusting a blood analysis algorithm of the monitor based upon the cuff parameter to optimize non-invasive blood pressure readings taken by the respective cuff.

8. The method of claim 7, further comprising the steps of:
    assigning a patient parameter to each blood pressure cuff, the patient parameter providing identification information for the patient wearing the respective cuff.

9. The method of claim 7, further comprising electronically communicating the cuff parameter to a medical record database.

10. The method of claim 8, further comprising electronically communicating the patient parameter to a medical records database.

11. The method of claim 7, wherein the blood pressure cuff is arranged to be worn about a wrist of the patient.

* * * * *